United States Patent [19]

Kolts et al.

[11] Patent Number: 4,613,722
[45] Date of Patent: Sep. 23, 1986

[54] DEHYDROGENATION OF $C_3$ AND $C_4$ HYDROCARBONS OVER AN IRON-BASED CATALYST

[75] Inventors: John H. Kolts, Ochelata; Gary A. Delzer, Bartlesville, both of Okla.

[73] Assignee: Phillips Petroleum Company, Bartlesville, Okla.

[21] Appl. No.: 758,940

[22] Filed: Jul. 25, 1985

[51] Int. Cl.$^4$ ............................................. C07C 4/02
[52] U.S. Cl. .................................. 585/651; 585/653; 585/661
[58] Field of Search ..................... 585/651, 653, 661

[56] References Cited

U.S. PATENT DOCUMENTS

| | | | |
|---|---|---|---|
| 2,415,477 | 2/1947 | Folkins et al. | 585/651 |
| 3,644,557 | 2/1972 | Senes et al. | 585/651 |
| 3,751,514 | 8/1973 | Hoppstock et al. | 585/653 |
| 3,751,516 | 8/1973 | Frech et al. | 585/653 |
| 3,766,278 | 10/1973 | Bogart et al. | 585/651 |
| 4,087,350 | 5/1978 | Kolombos et al. | 585/653 |
| 4,093,536 | 6/1978 | Heckelsberg | 585/653 |
| 4,152,300 | 5/1979 | Riesser | 502/324 |
| 4,159,970 | 7/1979 | Heckelsberg | 502/324 |
| 4,471,151 | 9/1984 | Kolts | 585/651 |

FOREIGN PATENT DOCUMENTS

| | | | |
|---|---|---|---|
| 47-42703 | 12/1972 | Japan | 585/653 |
| 1306087 | 2/1973 | United Kingdom | 585/651 |
| 0422165 | 8/1974 | U.S.S.R. | 585/651 |
| 0626111 | 9/1978 | U.S.S.R. | 585/651 |

Primary Examiner—John Doll
Assistant Examiner—Lance Johnson
Attorney, Agent, or Firm—C. F. Steininger

[57] ABSTRACT

Compositions of matter, including: a composition consisting of iron oxide and magnesium oxide; a composition comprising iron oxide, manganese oxide and magnesium oxide; a composition comprising a small amount of iron oxide and a larger amount of an oxide of a Lanthanum Series metal, particularly lanthanum and cerium; and a composition comprising iron oxide and niobium oxide. The above compositions are particularly useful as catalytic compositions for the conversion of $C_3$ and $C_4$ hydrocarbons to less saturated hydrocarbons, particularly ethylene and propylene and preferably ethylene, in the presence of steam. The steam substantially increases the active life of the catalytic composition, before regeneration is necessary, as well as significantly increasing the selectivity to ethylene. Limiting the amount of bound or fixed sulfur in the catalytic compositions also improves the catalysts.

16 Claims, No Drawings

DEHYDROGENATION OF $C_3$ AND $C_4$ HYDROCARBONS OVER AN IRON-BASED CATALYST

The present invention relates to improved compositions of matter. In a more specific aspect, the present invention relates to improved catalysts for the conversion of $C_3$ and $C_4$ hydrocarbons to less saturated hydrocarbons. In a more specific aspect, the present invention relates to improved catalysts for the conversion of $C_3$ and $C_4$ alkanes to less saturated hydrocarbons, particularly ethylene and propylene and preferably ethylene.

BACKGROUND OF THE INVENTION

Olefins, such as ethylene and propylene, have become major feedstocks in the organic chemical and petrochemical industries. Of these, ethylene is by far the most important chemical feedstock, since the requirements for ethylene feedstocks are about double those for propylene feedstocks. Consequently, improved methods for the conversion of less valuable hydrocarbons to ethylene and propylene, and particularly to ethylene, are highly desirable.

Numerous suggestions have been made for the production of ethylene and propylene, particularly ethylene, from various feedstocks and by a wide variety of processes.

At the present time, ethylene is produced almost exclusively by dehydrogenation or thermal cracking of ethane and propane, naphtha and, in some instances, gas oils. About 75% of the ethylene currently produced in the United States is produced by steam cracking of ethane and higher normally gaseous hydrocarbon components of natural gas, since natural gas contains from about 5 vol.% to about 60 vol.% of hydrocarbons other than methane. However, in most instances, the content of ethane and higher normally gaseous hydrocarbon materials in natural gas is less than about 25% and usually less than about 15%. Consequently, these limited quantities of feedstocks, which are available for the production of ethylene and propylene, and particularly etheylene, must be utilized efficiently. Unfortunately, these processes result in low conversions to olefins and selectivity to ethylene, as opposed to propylene, is poor. In addition, relatively severe conditions, particularly temperatures in excess of about 1000° C., are required and such processes are highly energy intensive.

In order to reduce the severity of the conditions and, more importantly, to improve the conversion of normally gaseous feedstocks to ethylene and propylene and selectivity to ethylene, numerous processess involving the use of solid contact materials have been proposed. Some of these proposals utilize inert solid contact materials to improve contact between the feed hydrocarbons and steam and also to maintain a more even temperature throughout the zone of reaction. In other instances, the solid contact material is catalytic in nature. Such use as solid contact materials, particularly catalysts, have resulted in modest improvements in conversion to ethylene and propylene but the selectivity to ethylene is improved very little. It is, therefore, highly desirable that improved catalytic processes be developed, particularly processes which increase the selectivity to ethylene, as opposed to propylene. However, little is understood concerning the manner in which such catalysts function, why certain components are effective while similar components are ineffective, or why certain combinations of components are effective and other combinations are not. Obviously, a number of theories have been proposed by workers of the art, but this only addes to the confusion, since it appears that each theory explains why a particular catalytic material works well, but does not explain why similar catalytic materials do not work and why other dissimilar materials are effective. As a result, the art of catalytic conversion of hydrocarbons to olefins remains highly unpredictable.

SUMMARY OF THE INVENTION

It is therefore an object of the present invention to provide improved compositions of matter and methods of utilizing the same, which overcome the above and other disadvantages of the prior art. Another object of the present invention is to provide improved compositions of matter. Still another object of the present invention is to provide improved catalytic compositions for the conversion of $C_3$ and $C_4$ hydrocarbons to less saturated hydrocarbons. Another and further object of the present invention is to provide an improved method for the conversion of $C_3$ and $C_4$ hydrocarbons to less saturated hydrocarbons, in the presence of steam. Yet another object of the present invention is to provide an improved process for the conversion of $C_3$ and $C_4$ hydrocarbons to less saturated hydrocarbons, in the presence of steam, to selectively produce ethylene, ethane and propylene, and particularly ethylene. A further object of the present invention is to provide an improved catalytic material for the conversion of $C_3$ and $C_4$ hydrocarbons to less saturated hydrocarbons, which has an improved effective life, before regeneration is necessary, particularly for the production of ethylene, ethane and propylene, and more particularly ethylene.

The present invention provides improved compositions of matter, including: a composition of matter consisting of iron oxide and magnesium oxide; a composition of matter comprising iron oxide, manganese oxide and magnesium oxide; and compositions of matter comprising iron oxide and at least one oxide of Lanthanum Series metals, particularly lanthanum and cerium, or niobium. These compositions of matter have been found to be highly effective catalyst compositions for the conversion of feed hydrocarbons comprising at least one of $C_3$ and $C_4$ hydrocarbons to less saturated hydrocarbons, in the presence of steam. A method of converting feed hydrocarbons comprising $C_3$ and $C_4$ hydrocarbons to less saturated hydrocarbons, particularly ethylene and propylene, and preferably ethylene, is provided in which the feed hydrocarbons are contacted with the above-mentioned catalytic compositions, in the presence of steam, under conditions sufficient to convert the feed hydrocarbons to less saturated product hydrocarbons. The effectiveness of the catalytic compositions is also improved by limiting the sulfur content thereof.

DETAILED DESCRIPTION OF THE INVENTION

The hydrocarbon feed components, in accordance with the present invention, can include any normally gaseous hydrocarbon stream containing significant amounts of $C_3$ and $C_4$ hydrocarbons, particularly propane and n-butane, with n-butane being preferred. The presence of other normally gaseous components or even normally liquid components, which vaporize at operating conditions, are not detrimental to the process. For example, it has been found that if isobutane is utilized, in accordance with the present invention, the catalysts of the present invention shift the product stream from isobutene to propylene and, therefore, one of the desired products of the present invention is produced. On the other hand, it has been found that the catalytic process of the present invention is generally ineffective, as compared with a strictly thermal process, in improving the conversion of ethane to ethylene. However, the presence of ethane in feed hydrocarbons, obviously, is not detrimental. Components other than hydrocarbons are also not detrimental. The primary criteria in all cases is the cost or difficulty of separating inert materials or the products of components other than $C_3$ and $C_4$ hydrocarbons from the desired ethylene and propylene and whether such separation is less costly and/or less difficult before or after conduct of the process of the present invention. Suitable feedstocks for the process of the present invention can be obtained from any source, including natural gas, refinery off-gases and the like. However, the most convenient and abundant source is $C_3$ and $C_4$ hydrocarbon streams recovered during the processing of a natural gas to produce a pipeline gas for heating purposes. Conventionally, $C_2$ and higher hydrocarbons are separated from methane to produce a pipeline gas for heating purposes, which predominates in methane, by compression and expansion, cryogenic means or a combination of both. Usually, the natural gas, either at a high pressure as produced or compressed to a high pressure, is treated to successively condense first normally liquid hydrocarbons ($C_6+$ hydrocarbons or natural gasoline), then $C_5$, followed by $C_4$, then $C_3$ and, finally, $C_2$ hydrocarbons, by cooling to successively lower temperatures with the separation or fractionation of the condensed liquid from uncondensed vapor between cooling stages. Thus, individual streams predominating in an individual hydrocarbon, such as $C_5$, $C_4$, $C_3$ and $C_2$, can be obtained or streams predominating in combinations of the individual hydrocarbons can be recovered. Accordingly, the thus separated propane stream or the thus separated butanes stream can be be utilized as a feed hydrocarbon for the present invention, or a stream predominating in a mixture of propane and butanes can be utilized. Obviously, the latter would eliminate the necessity of one stage of cooling and separation in a natural gas processing system.

The compositions of matter of the present invention include a composition consisting of an oxide of iron and an oxide of magnesium; a composition comprising an oxide of iron, an oxide of manganese, and an oxide of magnesium; a composition comprising a minor amount of an oxide of iron, a major amount of an oxide of a metal of the Lanthanum Series, preferably lanthanum or cerium; and a composition comprising an oxide of iron and an oxide of niobium. From time to time, herein, the iron oxide and the manganese oxide are referred to as promotors or active components and the magnesium oxide, Lanthanum Series oxide or niobium oxide as a base material. This reference is simply as a matter of convenience, because the iron oxide and/or the manganese oxide are usually the minor components and the magnesium oxide, the Lanthanum Series oxides and the niobium oxide are major components. Accordingly, it is to be understood that such reference is not meant to categorize the components. As will appear hereinafter, all the recited components are necessary and are catalytically active in the process of the present invention.

The above mentioned compositions of matter have been found to be particularly effective as catalytic compositions for the conversion of $C_3$ and $C_4$ hydrocarbons to less saturated hydrocarbons. Accordingly, for such use, the composition will generally contain from about 0.1 to about 30 wt.% of iron, expressed as elemental iron based on the total weight of the composition, and preferably between about 0.5 and about 15 wt.% of iron. Similar amounts of manganese or iron can be utilized as a combination of iron oxide and manganese oxide on a magnesium oxide base. However, such amounts of iron and manganese may be reduced where the combination is utilized.

The method of preparation of the catalyst compositions of the present invention does not appear to be critical, so long as the desired final compositions of the component metal ozides is obtained. Suitable methods of preparation include slurry blending, solution blending, dry blending, impregnation and co-precipitation, all of which are well known to those skilled in the art. A convenient method is to add metal solids, such as, MgO or Mg(OH)$_2$, of the base material to a blending apparatus along with an aqueous solution of a metal salt, such as ferric nitrate, of the promoter and mixing for several minutes, for example, 2–5 minutes, to form a thick slurry. In the interest of economy, excess water should be avoided. The resulting slurry is then dried in air by conventional means, at about 100° C. to 150° C., calcined for about four hours, at about 750° C. to 800° C., and then ground, sieved and, optionally, pelleted or otherwise sized by means well known in the art.

When utilizing the above-mentioned catalyst composition, containing iron oxide, it has been found, in accordance with another aspect of the present invention, that steam is essential to the conduct of the process. Specifically, the presence of steam, during a conduct of the conversions of $C_3$ and $C_4$ hydrocarbons, greatly extends the active life of the catalyst and it has been found that, without steam, over an extended period of time, the iron oxide reduces to metallic iron, which is ineffective in the process.

The process of the present invention can be carried out in fixed, moving, fluidized, ebulating or entrained bed reactors. For experimental purposes and, obviously, to permit accurate measurement and precise control of the process variables, the runs hereinafter set forth in the examples were conducted in a fixed bed reactor.

During operation, in accordance with the present invention, it has been found that small amounts of the feedstock are converted to coke, which is then desposited upon the catalyst and contributes to a decline in the catalyst activity, particularly the selectivity to ethylene. Accordingly, it is desirable to periodically regenerate the catalyst by conventional techniques of carbon removal, such as treatment with an oxygen-containing gas, such as air. During such regeneration, it may also be desirable to use inert gas or steam dilution to control burn-off temperature, as is also well known to those skilled in the art.

Following preparation of the catalytic composition, the catalyst may be prepared for use by purging with an inert gas, such at nitrogen. Normally, the catalyst would be disposed in the reactor and be brought up to reaction temperature by preheating with air, then purging with hot nitrogen and, finally, introducing the hydrocarbon feed. Since it is preferred that steam be added to the hydrocarbon feed, in the conduct of the process of the present invention, it may be preferred to use steam rather than nitrogen as a purging gas. The catalyst may also, optionally, be pretreated with hydrogen before use. Such treatment is preferably carried out at about the operating temperature of the process and at a pressure up to about 600 psia. Such hydrogen pretreatment appears to reduce higher oxidation states of manganese and/or iron and, thereby, reduces initial carbon oxide formation.

With the exception of the presence of steam and the possible exception of the temperature of operation, the operating conditions of the process, in accordance with the present invention, do not appear to be highly critical. Accordingly the following conditions of operation are those found effective and preferred.

The steam/hydrocarbon mol ratio may be between about 0.1/1 to about 10/1 and is preferably between about 0.5/1 and about 5/1.

The hydrocarbon gas hourly space velocity (GHSV) may range from about 100 to about 3000 but is preferably between about 500 and about 1000.

The operating pressure may be between about 0.1 at about 100 psia and is preferably between about 1 and about 60.

The temperature of operation appears to be significant in the conversion of feed hydrocarbons to olefins and particularly in improving the selectivity to ethylene. Suitable temperatures range between about 550° C. and about 850° C., with the preferred range being between about 650° C. and about 775° C.

The nature and advantages of the present invention are illustrated by the following examples.

EXAMPLE I

Quartz chips were utilized for a comparative run representive of thermal cracking in the presence of steam. All catalysts, in general, were prepared either by incipient wetness impregnation of the support oxides or co-precipitation from various soluble materials. The promoting materials were in their oxide form but their concentrations are reported as weight percent of elemental metal based on the total weight of the catalyst.

The reactor was a fixed bed 18 mm (i.d.) quartz reactor which held 25 cc of catalyst. The reactor contained a quartz thermocouple well centered axially along the catalyst bed and the temperatures reported are the longitudinal midpoint in the catalyst bed.

In the experiments reported, all catalysts were pretreated in the same manner. This pretreatment involved air oxidation for 10 min., nitrogen purge for 2 min., hydrogen reduction for 10 min. and a final nitrogen purge. The catalyst was brought up to reaction temperature prior to the introduction of the hydrocarbon feed. The hydrocarbon feed was n-butane at a flow rate of 100 cc/min. through a water saturator at about 81° C. The combined feed plus steam flow rate resulted in approximately a 1 second residence time through the catalyst bed.

Effluent from the reactor was snap sampled and analyzed by chromatographic techniques. Product sampling was normally after 2–5 min. of feed. This reaction time determines the "initial activity" of a catalyst. The conversion is reported as mol percent of n-butane converted and the conversion level was maintained at 50 mol % for comparative purposes. The reported selectivities are based on normalized mols of feed converted to the indicated products.

The results of this series of runs is reported in the following table.

TABLE 1

| Catalyst | Temp. °C. | Conv. | Selectivity $C_2=$ | $C_3=$ | $C_2$ | $\frac{C_2= + C_2}{C_3=}$ |
|---|---|---|---|---|---|---|
| Quartz-Chips | 720 | 50 | 30 | 39 | 7 | 0.95 |
| 5% Fe/MgO | 675 | 50 | 31 | 26 | 19 | 1.92 |
| 5% Fe/CaO | 705 | 50 | 30 | 34 | 10 | 1.17 |
| 3.5% Co/MgO | 708 | 50 | 30 | 38 | 7 | 0.97 |
| 5% Fe/La$_2$O$_3$ | 672 | 50 | 18 | 21 | 14 | 1.52 |
| 4% Fe/CeO$_2$* | 645 | 50 | 22 | 16 | 22 | 2.75 |
| 5% Co/La$_2$O$_3$** | 542 | 50 | — | — | 3 | — |

*14% Selectivity to Butenes
**77% Selectivity to Methane

It is to be observed from the above table that the combinations of iron oxide/magnesium oxide; iron oxide/lanthanum oxide; and iron oxide/cerium oxide, in accordance with the present invention, are substantially superior to the thermal conversion in the presence of quartz chips, in the selectivity to $C_2$ hydrocarbons and particularly the conversion to $C_2$ hydrocarbons, as opposed to propylene. Specifically the thermal conversion will generally result in a $C_2$/propylene ratio of about 1. On the other hand, when utilizing catalyst materials of the present invention, this ratio is at least 1.5, and generally 2 or more.

Since cobalt is generally considered an equivalent catalytic material to iron, comparative tests were also made with cobalt oxide on magnesium oxide and cobalt oxide on lanthanum oxide. It is to be seen that the cobalt on magnesium oxide was no better than the thermal cracking operation and the cobalt on lanthanum oxide was essentially useless for any purpose. In order to illustrate the fact that magnesium oxide is the only effective base of Group IIA metals, a comparison was run utilizing iron oxide on calcium oxide as a base. Here again, the results indicate that this combination is little better than the thermal conversion run.

As previously pointed out, the presence of steam, during the conduct of the reaction, not only increases the life of the catalyst compositions of the present invention but is necessary to obtain the desired results of the present process. The following example illustrates this.

EXAMPLE II

A series of isothermal runs were made for n-butane cracking, utilizing a catalyst composition having 4 wt.% of iron (expressed in terms of elemental iron based on the total weight of the catalyst) on a magnesium oxide base. The catalyst was prepared by wet slurrying. 17 cc of catalyst was disposed in an 18 mm (i.d.) quartz reactor. The n-butane feed rate was about 100 cc/min., thus providing a 1 second residence time when the steam/hydrocarbon ratio was 1/1. The residence time was proportionately less for larger steam/hydrocarbon ratios. Temperatures were maintained at 709° C., 713° C., 716° C. and 722° C. for hydrocarbon/steam ratios of 1/1, ½, ⅓ and a nitrogen/hydrocarbon ratio of 1/1 respectively.

Hydrogen production is reported since the hydrogen production is proportional to the amount of carbon formed, which in turn indicates the degree of catalyst fouling or inactivation.

The results of this series of tests are set forth in the following table.

TABLE 2

| Feed/Diluent | On-Stream Time, min. | Conv. % | Selectivity, % $C_2=$ | $C_3=$ | $C_2$ | $C_4=$ | Selectivity Ratio, $C_2=/C_3=$ | % $H_2$ |
|---|---|---|---|---|---|---|---|---|
| 1:1 (Steam) | 5 | 60 | 37 | 25 | 16 | 2 | 1.48 | 20 |
| 1:1 (Steam) | 10 | 57 | 36 | 28 | 13 | 2 | 1.29 | 21 |
| 1:1 (Steam) | 20 | 56 | 35 | 28 | 12 | 3 | 1.25 | 22 |
| 1:1 (Steam) | 40 | 51 | 30 | 37 | 8 | 4 | 0.81 | 17 |
| 1:2 (Steam) | 5 | 52 | 38 | 27 | 13 | 2 | 1.41 | 20 |
| 1:2 (Steam) | 40 | 47 | 38 | 29 | 11 | 3 | 1.31 | 18 |
| 1:2 (Steam) | 75 | 45 | 37 | 31 | 10 | 3 | 1.19 | 18 |
| 1:2 (Steam) | 120 | 45 | 34 | 35 | 8 | 3 | 0.97 | 17 |
| 1:2 (Steam) | 155 | 45 | 32 | 27 | 8 | 4 | 0.86 | 15 |
| 1:3 (Steam) | 5 | 43 | 40 | 27 | 13 | 2 | 1.48 | 19 |
| 1:3 (Steam) | 44 | 45 | 39 | 28 | 11 | 2 | 1.39 | 18 |
| 1:3 (Steam) | 80 | 44 | 39 | 29 | 11 | 2 | 1.34 | 17 |
| 1:3 (Steam) | 122 | 41 | 39 | 30 | 10 | 2 | 1.30 | 16 |
| 1:3 (Steam) | 175 | 40 | 38 | 31 | 9 | 3 | 1.23 | 18 |
| 1:3 (Steam) | 255 | 39 | 36 | 33 | 8 | 3 | 1.09 | 16 |
| 1:3 (Steam) | 294 | 38 | 35 | 34 | 8 | 3 | 1.03 | 15 |
| 1:3 (Steam) | 360 | 40 | 34 | 35 | 8 | 4 | 0.97 | 14 |
| 1:1 ($N_2$) | 5 | 46 | 25 | 22 | 20 | 4 | 1.14 | 44 |
| 1:1 ($N_2$) | 10 | 43 | 23 | 27 | 15 | 4 | 0.85 | 41 |
| 1:1 ($N_2$) | 20 | 35 | 29 | 34 | 9 | 5 | 0.85 | 24 |

Inspection of the data of the above table shows quite clearly that the catalyst life is extended significantly by the utilization of steam, particularly at the higher ratios. In addition, the selectivity to ethylene, as opposed to propylene, is significantly improved both at the start of the process cycle and over an extended period of time. For example, at a 1/1 hydrocarbon/steam ratio the selectivity of ethylene/propylene is greater than 1 for about 30 min., at a ⅓ hydrocarbon/steam ratio the selectivity remains about 1.4 about 300 min., and when utilizing nitrogen the ratio drops below 1 in less than 10 min.

In the run utilizing nitrogen instead of steam, it is also to be seen that hydrogen production was at least double that when utilizing steam. Finally, when nitrogen was used, conversion of n-butane was initially as low as any of the runs with steam and dropped rapidly below any of the runs with steam in less than about 20 minutes.

Another series of runs was conducted compared with thermal conversion (one quartz chips) at varying temperatures.

EXAMPLE III

The catalyst in the present example was prepared by slurrying, to produce a catalytic material containing 4% elemental iron as iron oxide on a magnesium oxide base. The steam/hydrocarbon ratio was 1/1. Otherwise, the conditions of operation were the same as those in the previous examples. The times at which the sample was taken after the beginning of hydrocarbon feed and steam are set forth in the Table.

TABLE 3

| Catalyst | Min. | Temp | Conv. | Selectivities $C_2=$ | $C_3=$ | $C_2$ | $\frac{C_2= + C_2}{C_3=}$ |
|---|---|---|---|---|---|---|---|
| Quartz Chips | 4 | 602 | 5 | 22 | 50 | 10 | 0.64 |
|  | 4 | 627 | 11 | 24 | 48 | 8 | 0.67 |
|  | 4 | 642 | 19 | 25 | 46 | 8 | 0.69 |
|  | 4 | 666 | 24 | 29 | 45 | 6 | 0.73 |
|  | 5 | 684 | 33 | 27 | 44 | 8 | 0.80 |
|  | 4 | 718 | 65 | 33 | 36 | 6 | 1.08 |
|  | 4 | 743 | 81 | 38 | 30 | 6 | 1.46 |
|  | 4 | 767 | 92 | 44 | 23 | 5 | 2.13 |
| 4% Fe/MgO | 2 | 617 | 13 | 27 | 25 | 21 | 1.92 |
|  | 3 | 639 | 19 | 32 | 26 | 23 | 2.12 |
|  | 3 | 661 | 31 | 33 | 24 | 22 | 2.29 |
|  | 3 | 686 | 46 | 34 | 25 | 20 | 2.16 |
|  | 3 | 697 | 48 | 37 | 25 | 19 | 2.24 |
|  | 3 | 709 | 59 | 36 | 23 | 19 | 2.39 |
|  | 3 | 735 | 74 | 38 | 21 | 15 | 2.52 |

It is to be observed from Table 3 that the thermal conversion resulted in substantially lower conversions, substantially lower selectivity to $C_2$ hydrocarbons, as opposed to propylene, and substantially lower selectivities to ethylene, as opposed to propylene. The only run in which the thermal conversion even approached the results obtained in accordance with the catalytic process of the present invention was the last run in which a $C_2$/propylene ratio of 2.13 was obtained. However, it should be clearly observed that this ratio is obtained only at a temperature nearly 130° higher than the same ratio could be obtained in accordance with the present invention.

The following example illustrates the effectiveness of a catalyst composition comprising iron oxide deposited on a cerium oxide base at various temperatures, again compared with a thermal conversion with quartz chips.

EXAMPLE IV

This series of tests was conducted in substantially the same manner and under substantially the same conditions as previous tests, utilizing a catalyst composition comprising 4 wt.% iron (expressed in terms of elemental iron based on the total weight of the catalyst) on a cerium oxide base. The feed hydrocarbon was n-butane, the conditions of operation were generally the same as previously utilized, with a feed hydrocarbon rate of 100 cc/min. and a steam/hydrocarbon ratio of 1/1.

The results of this series of runs is set forth in Table 4 below.

TABLE 4

| Catalyst | Temp. °C. | Conv. | Selectivity $C_2=$ | $C_3=$ | $C_2$ | $\frac{C_2= + C_2}{C_3=}$ |
|---|---|---|---|---|---|---|
| Quartz Chips | 625 | 14 | 24 | 46 | 9 | 0.67 |
|  | 643 | 19 | 25.1 | 46.1 | 8.5 | 0.73 |
|  | 650 | 21 | 26 | 46 | 8 | 0.74 |
|  | 676 | 27.4 | 29.1 | 43.7 | 6.2 | 0.81 |
|  | 697 | 52.8 | 29.7 | 39.1 | 7.8 | 0.93 |
| 4% Fe/CeO$_2$ | 625 | 22 | 21 | 14 | 20 | 2.93 |
|  | 629 | 32.8 | 21.6 | 14.6 | 21 | 2.92 |

TABLE 4-continued

| Catalyst | Temp. °C. | Conv. | Selectivity $C_2=$ | $C_3=$ | $C_2$ | $\frac{C_2= + C_2}{C_3 =}$ |
|---|---|---|---|---|---|---|
| | 647 | 50.1 | 22 | 15.9 | 21.4 | 2.73 |
| | 650 | 55 | 22 | 16 | 22 | 2.75 |
| | 668 | 70.5 | 21.3 | 16.2 | 22.5 | 2.70 |

The above table clearly illustrates that the catalytic process of the present invention dramatically reduces the production of propylene and dramatically increases the selectivity to $C_2$ hydrocarbons, as opposed to propylene. While not shown, the catalytic process also dramatically reduces methane production and substantially increases the production of mixed butenes which, of course, are also desirable products. The data also indicate typical results which are obtained by thermal cracking over the temperature range of operation of the catalytic process of the present invention.

In parallel work it has been found that the addition of small promoting amounts of calcium, strontium or barium to certain catalysts were effective in increasing the life and the selectivities to olefins, particularly ethylene, when cracking $C_3$ and $C_4$ hydrocarbons. The following example illustrates that these promotors are essentially ineffective in catalytic materials which include iron oxides.

EXAMPLE V

This series of runs was conducted in the presence of a catalyst comprising 3 wt.% calcium and 4 wt.% iron (expressed in terms of elemental metal based on the total weight of a catalyst) combined with a magnesium oxide base. The catalyst was prepared by the previously mentioned slurrying technique. All runs were made under essentially the same conditions as previous runs. The time given in the following table is the sample time after hydrocarbon feed was started and the temperature was, as previously indicated, the midpoint temperature of the catalyst bed.

TABLE 5

| Catalyst | Min. | °C. Temp. | Conv. | Selectivities $C_2=$ | $C_3=$ | $C_2$ | $\frac{C_2= + C_2}{C_3 =}$ | % H2 |
|---|---|---|---|---|---|---|---|---|
| 3% Ca/4% Fe/MgO | 5 | 608 | 6 | 23 | 48 | 11 | 0.71 | 3 |
| | 5 | 631 | 10 | 25 | 45 | 11 | 0.80 | 5 |
| | 5 | 657 | 20 | 27 | 42 | 11 | 0.90 | 9 |
| | 6 | 672 | 35 | 29 | 38 | 10 | 1.03 | 13 |
| | 5 | 706 | 52 | 31 | 34 | 9 | 1.18 | 18 |
| | 5 | 729 | 71 | 34 | 29 | 8 | 1.45 | 22 |

It is to be observed that the data of the above table indicate that the combination of calcium oxide/iron oxide and magnesium oxide, as a catalyst, was no better than the thermal conversion obtained in the presence of quartz chips and which are set forth in the previous examples. Selectivity to ethylene, as opposed to propylene, was poor, selectivity to $C_2$ hydrocarbons, as opposed to propylene, was low, and the catalyst tended to coke considerably, particularly at higher temperatures. For example, at 52% conversion of n-butane the calcium/iron/magnesium oxide catalyst resulted in a $C_2$/propylene ratio of only 1.18. On the other hand, an iron/magnesium oxide catalyst (Table 1) at the same conversion and a lower temperature, resulted in a ratio of 1.92. A $C_2$/propylene ratio significantly above 1.00 was not obtained except at 729° C., which is typical of a thermal conversion process and which was substantially less than the ratio obtained at a temperature of about 110° less with the iron oxide/magnesium oxide catalyst as shown by the results of Table 3.

It is also highly desirable, in accordance with the present invention, to limit the amount of "bound" or "fixed" sulfur in the components used to prepare the catalysts of the present invention. It appears that the presence of such bound or fixed sulfur in the catalytic material tends to inhibit the selectivity of the catalyst for the production of $C_2$ hydrocarbons. Such sulfur is referred to as "bound" or "fixed" sulfur, since it does not appear to be converted to hydrogen sulfide or to be otherwise lost during the hydrocarbon conversion process or the regeneration step and is probably present in sulfate form. Desirably, the sulfur content should be below about 0.2 wt.%, expressed in terms of elemental sulfur based on the total weight of catalyst, and preferably below about 0.1 wt. %.

While specific materials, conditions of operation, modes of operation and equipment have been referred to herein, it is to be recognized that these and other specific recitals are for illustrative purposes and to set forth the best mode only and are not to be considered limiting.

That which is claimed is:

1. A method for converting feed hydrocarbons comprising at least one of $C_3$ and $C_4$ hydrocarbons to less saturated product hydrocarbons, comprising:
   contacting feed hydrcarbons comprising at least one of $C_3$ and $C_4$ hydrocarbons, in the presence of steam, with a catalyst composition selected from the group consisting of:
   (a) a catalyst composition consisting essentially of: (1) a minor amount of at least one oxide of iron and (2) a major amount of at least one oxide of magnesium;
   (b) a catalyst composition consisting essentially of (1) a minor amount of at least one oxide of iron, (2) a minor amount of at least one oxide of manganese and (3) a major amount of at least one oxide of magnesium;
   (c) a catalyst composition comprising: (1) a minor amount of at least one oxide of iron and (2) a major amount of at least one oxide of at least one metal of the Lanthanum Series; and
   (d) a catalyst composition comprising: (1) a minor amount of at least one oxide of iron and (2) a major amount of at least one oxide of niobium,
   under conditions sufficient to convert said feed hydrocarbons to said less saturated product hydrocarbons.

2. A method in accordance with claim 1 wherein the feed hydrocarbons comprise propane.

3. A method in accordance with claim 1 wherein the feed hydrocarbons comprise butanes.

4. A method in accordance with claim 1 wherein the feed hydrocarbons comprise a mixture of propane and butanes.

5. A method in accordance with claim 1 wherein the conditions are sufficient to selectively convert the feed hydrocarbons to ethylene and ethane.

6. A method in accordance with claim 5 wherein the conditions are sufficient to selectively convert the feed hydrocarbons to ethylene.

7. A method in accordance with claim 1 wherein catalyst compositions (a), (b), (c) and (d) contain iron in an amount between about 0.1 and 30 wt.%, expressed in terms of elemental iron based on the total weight of said catalyst.

8. A method in accordance with claim 1 wherein the catalyst composition consists essentially of: (1) at least one oxide of iron and (2) at least one oxide of magnesium.

9. A method in accordance with claim 1 wherein the catalyst composition consists essentially of: (1) at least one oxide of iron, (2) at least one oxide of manganese and (3) at least one oxide of magnesium.

10. A method in accordance with claim 9 wherein the catalyst composition contains between about 0.1 and about 30 wt.% of manganese, expressed in terms of elemental manganese based on the total weight of said catalyst.

11. A method in accordance with claim 1 wherein the catalyst composition comprises: (1) at least one oxide of iron and (2) at least one oxide of at least one metal of the Lanthanum Series.

12. A method in accordance with claim 11 wherein the metal of the Lanthanum Series is selected from the group consisting of lanthanum and cerium.

13. A method in accordance with claim 1 wherein the catalyst composition comprises: (1) at least one oxide of iron and (2) at least one oxide of niobium.

14. A method in accordance with claim 1 wherein the temperature is maintained between about 550° C. and about 850° C.

15. A method in accordance with claim 1 wherein the steam/feed hydrocarbon ratio is maintained between about 0.1/1 and about 10/1.

16. A method in accordance with claim 1 wherein the sulfur content of catalyst compositions (a), (b), (c) and (d) is below about 0.2 wt.%, expressed in terms of elemental sulfur based on the total weight of said catalyst.

* * * * *